United States Patent [19]

Galbo et al.

[11] Patent Number: 4,921,962
[45] Date of Patent: May 1, 1990

[54] PROCESS FOR PREPARING N-HYDROCARBYLOXY DERIVATIVES OF STERICALLY HINDERED AMINES

[75] Inventors: James P. Galbo, Hartsdale; Michael H. Ackerman, New City, both of N.Y.

[73] Assignee: Ciba-Geigy Corporation, Ardsley, N.Y.

[21] Appl. No.: 259,949

[22] Filed: Oct. 19, 1988

[51] Int. Cl.$^5$ .............................................. C07D 211/94
[52] U.S. Cl. ...................................... 546/184; 546/16; 546/188; 546/192; 548/408; 548/542
[58] Field of Search ............... 546/184, 16, 192, 188; 548/408, 542; 540/466, 543

[56] References Cited

U.S. PATENT DOCUMENTS 4,581,429 4/1986 Solomon .............................. 548/542
4,665,185 5/1987 Winter et al. ....................... 546/184

Primary Examiner—Donald G. Daus
Attorney, Agent, or Firm—Luther A. R. Hall

[57] ABSTRACT

N-hydrocarbyloxy compounds of the formula

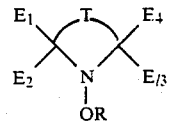

where $E_1$, $E_2$, $E_3$ and $E_4$ are independently an organic radical so that the carbon atoms to which they are attached are each a quaternary carbon, R is a hydrocarbon radical and T is a divalent radical are prepared directly by the reaction of the corresponding amine or oxyl compound in a hydrocarbon organic solvent with a hydroperoxide in the presence of a metal carbonyl, metal oxide or metal alkoxide catalyst in high yield and purity. These compounds are useful as light stabilizers in diverse substrate systems.

11 Claims, No Drawings

PROCESS FOR PREPARING N-HYDROCARBYLOXY DERIVATIVES OF STERICALLY HINDERED AMINES

The instant invention pertains to a process for preparing N-hydrocarbyloxy derivatives of sterically hindered amines direct from the corresponding amine or from the corresponding N-oxyl intermediate.

BACKGROUND OF THE INVENTION

Representative N-hydrocarbyloxy derivatives of sterically hindered amines are described in copending U.S. patent application Ser. No. 259,950.

The ultimate starting materials for making the instant N-hydrocarbyloxy derivatives of the sterically hindered amines are the sterically hindered amines themselves. Other useful intermediates are the corresponding N-hydroxyl and N-oxyl compounds.

U.S. Pat. No. 4,665,185 describes a facile process for preparing said N-oxyl compounds by the direct oxidation of the sterically hindered amine in an inert organic solvent with a hydroperoxide in the presence of a metal carbonyl, metal oxide or metal alkoxide catalyst. The corresponding N-hydroxyl compounds can be made by the catalytic hydrogenation of the N-oxyl compounds.

OBJECTS OF THE INVENTION

One object of this invention is to provide a process for the production of N-hydrocarbyloxy compounds by the oxidation of sterically hindered secondary amines.

A further object of this invention is to provide a second process for the production of N-hydrocarbyloxy derivatives from the corresponding N-oxyl compounds.

DETAILED DESCRIPTION

The instant invention pertains to a process for the efficient preparation of N-hydrocarbyloxy derivatives of sterically hindered secondary amines by the oxidation of said amines or from the corresponding N-oxyl compounds using a hydroperoxide in the presence of a small amount of a metal ion catalyst in a hydrocarbon organic solvent at moderate temperatures to give the N-hydrocarbyloxy derivatives in high yield and purity.

Generically the instant invention is a process for the preparation of an N-hydrocarbyloxy compound of the formula

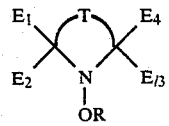

where the nitrogen atom is flanked by two quaternary carbon atoms, that is where $E_1$, $E_2$, $E_3$ and $E_4$ are independently an organic radical, R is a hydrocarbyl radical and T is a divalent group required to form a cyclic 5- or 6-membered ring which comprises
oxidizing an amine of the formula

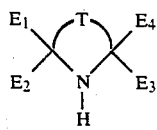

where $E_1$, $E_2$, $E_3$, $E_4$ and T have the meanings given above, dissolved in a hydrocarbon organic solvent with a hydroperoxide in the presence of from 0.001 to 0.1 mole percent, based on the hydroperoxide, of a catalyst selected from the group consisting of the metal carbonyls, the metal oxides, the metal acetylacetonates and the metal alkoxides where the metal is selected from groups IVb, Vb, VIb, VIIb and VIII of the periodic table, at a temperature of 50° to 200° C., preferably 75° to 160° C., with the mole ratio of hydroperoxide to amine being 50:1 to 2:1, preferably 10:1 to 3:1, with the reaction mixture being heated till color associated with the presence of N-oxyl compound disappears.

More specifically, the instant invention is a process for the preparation of an N-hydrocarbyloxy compound of the formula

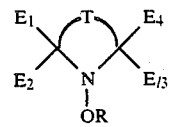

wherein
$E_1$ and $E_3$ are independently alkyl of 1 to 5 carbon atoms or phenyl,
$E_2$ and $E_4$ are independently alkyl of 1 to 5 carbon atoms, or
$E_1$ and $E_2$ together or $E_3$ and $E_4$ together or both $E_1$ and $E_2$ together and $E_3$ and $E_4$ together are tetramethylene or pentamethylene,
R is alkyl of 1 to 18 carbon atoms, cycloalkyl of 5 to 12 carbon atoms, hydrocarbyl radical of a saturated bicyclic or tricyclic hydrocarbon of 7 to 12 carbon atoms, aryl of 6 to 10 carbon atoms, aralkyl of 7 to 13 carbon atoms, or said aralkyl substituted by alkyl of 1 to 4 carbon atoms, and
T is a divalent group required to form a cyclic 5- or 6-membered ring.

Generically the instant invention is also a process for the preparation of an N-hydrocarbyloxy compound of the formula

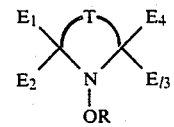

where the nitrogen atom is flanked by two quaternary carbon atoms, that is where $E_1$, $E_2$, $E_3$ and $E_4$ are independently an organic radical, R is a hydrocarbyl radical and T is a divalent group required to form a cyclic 5- or 6-membered ring which comprises
converting an oxyl compound of the formula

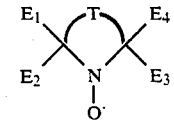

where $E_1$, $E_2$, $E_3$, $E_4$ and T have the meanings given above, dissolved in a hydrocarbon organic solvent with a hydroperoxide in the presence of from 0.001 to 0.1 mole percent, based on the hydroperoxide, of a catalyst selected from the group consisting of the metal carbonyls, the metal oxides, the metal acetylacetonates and the metal alkoxides where the metal is selected from groups IVb, Vb, VIb, VIIb and VIII of the periodic table, at a temperature of 50° to 200° C., preferably 75° to 160° C., with the mole ratio of hydroperoxide to N-oxyl compound being 50:1 to 2:1, preferably 10:1 to 2:1, with the reaction mixture being heated till color associated with the presence of N-oxyl compound disappears.

More specifically, the instant invention is a process for the preparation of an N-hydrocarbyloxy compound of the formula

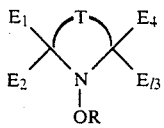

wherein $E_1$ and $E_3$ are independently alkyl of 1 to 5 carbon atoms or phenyl, $E_2$ and $E_4$ are independently alkyl of 1 to 5 carbon atoms, or $E_1$ and $E_2$ together or $E_3$ and $E_4$ together or both $E_1$ and $E_2$ together and $E_3$ and $E_4$ together are tetramethylene or pentamethylene, R is alkyl of 1 to 18 carbon atoms, cycloalkyl of 5 to 12 carbon atoms, hydrocarbyl radical of a saturated bicyclic or tricyclic hydrocarbon of 7 to 12 carbon atoms, aryl of 6 to 10 carbon atoms, aralkyl of 7 to 13 carbon atoms, or said aralkyl substituted by alkyl of 1 to 4 carbon atoms, and T is a divalent group required to form a cyclic 5- or 6-membered ring.

Preferably R is alkyl of 5 to 18 carbon atoms, and most preferably alkyl of 7 to 18 carbon atoms.

Preferably R is cycloalkyl of 5 to 12 carbon atoms, most preferably cyclopentyl, cyclohexyl, cyclooctyl, cyclododecyl or methylcyclohexyl.

Preferably R is aralkyl of 7 to 9 carbon atoms such as benzyl, alpha-methylbenzyl, o,alpha-dimethylbenzyl, m,alpha dimethylbenzyl, p,alpha-dimethylbenzyl or alpha,alpha-dimethylbenzyl. Most preferably R as aralkyl is alpha-methylbenzyl or alpha,alpha-dimethylbenzyl.

When R is alkyl, it is for example methyl, ethyl, butyl, amyl, hexyl, heptyl, octyl, nonyl, decyl, dodecyl, hexadecyl or octadecyl.

When R is cycloalkyl, it is for example cyclopentyl, cyclohexyl, methylcyclohexyl, cycloheptyl, cyclooctyl, cyclodecyl or cyclododecyl.

Preferably $E_1$, $E_2$, $E_3$ and $E_4$ are each methyl.

The nature of T is not critical to the instant process with the understanding that T remains inert, that is T remains chemically unchanged, to hydroperoxide attack.

The amines or N-oxyl compounds which can be oxidized or converted according to the invention contain a nitrogen atom which is substituted by two tertiary carbon atoms. Preferred compounds are cyclic amines having the two carbon atoms adjacent to the ring nitrogen fully substituted by alkyl groups.

The N-hydrocarbyloxy derivatives of the instant invention can be prepared by a number of routes.

These include the reaction of the corresponding hydroxylamine (N—OH) compound with sodium hydride and an active halogen compound such as benzyl bromide or ethyl iodide. The N-methoxy variants can be prepared by the thermolysis of a chlorobenzene solution of the corresponding N-oxyl compound and di-tert-butyl peroxide. The N-methoxy product is formed by a coupling reaction between the N-oxyl radical and the methyl radical generated from the beta-scission of the tert-butoxy radical.

However, the preferred method for preparing the instant N-hydrocarbyloxy derivatives and the focus of the instant invention is the reaction of a sterically hindered amine with aqueous hydroperoxide in the presence of a metal catalyst and a hydrocarbon solvent.

This is illustrated by the following example where 4-benzoyloxy-2,2,6,6-tetramethylpiperidine is reacted with aqueous tert-butyl hydroperoxide in the presence of molybdenum oxide in ethylbenzene solvent to give a 90% yield of 1-(alpha-methylbenzyloxy)-2,2,6,6-piperidin-4-yl benzoate.

Although the oxidation of sterically hindered amines with aqueous hydroperoxide in the presence of hydrocarbon solvent occurs without a catalyst, the yields of N-hydrocarbyloxy product are low, the reaction rate is slow and the final product is impure being contaminated with large amounts of unreacted N-oxyl intermediate. The oxidation of hindered amine to N-oxyl intermediate is much more rapid than the subsequent conversion of the N-oxyl intermediate to the N-hydrocarbyloxy derivative.

This subsequent conversion to N-hydrocarbyloxy derivative is greatly enhanced as to speed of reaction and efficiency of conversion if the reaction is carried out in the presence of a metal catalyst, especially the molybdenum (VI) catalysts.

When the sterically hindered amine is first treated with aqueous hydroperoxide in the presence of the catalyst in an inert organic solvent, the initial reaction product obtained in a relatively short time is the corresponding N-oxyl intermediate which is highly colored.

As is taught in U.S. Pat. No. 4,665,185, such N-oxyl compounds are useful in their own right and can be isolated per se as highly colored (usually bright red) compounds.

When the organic solvent in the instant invention is a hydrocarbon having a labile hydrogen atom, when there remains a sufficient molar excess of hydroperoxide beyond that needed to convert the amine to the corresponding N-oxyl derivative, and when the reaction mixture is heated at moderate temperatures (preferably 100°–150° C.) for an additional period, a further reaction takes place between the N-oxyl compound (either prepared in situ from the original amine or employed as the initial starting intermediate in the process) and the hydrocarbon solvent to give the corresponding N-hydrocarbyloxy derivative.

The original reaction mixture is colorless, but becomes highly colored as the N-oxyl intermediate is formed. This color disappears as the N-oxyl compound is converted into the colorless N-hydrocarbyloxy final product.

The instant process thus in essence has a built-in color indicator to show the extent of reaction. When the reaction mixture becomes colorless, it shows that the colored N-oxyl intermediate has been completely converted into the desired N-hydrocarbyloxy product.

The sterically hindered amine starting materials are largely items of commerce or can be prepared by methods known in the art from commercially available starting materials.

The corresponding N-oxyl intermediates are made from sterically hindered amines by the method described in U.S. Pat. No. 4,665,185.

In the reaction of converting a hindered amine N—H to the N-hydrocarbyloxy derivative, the molar ratio of hydroperoxide:amine is preferably 10:1 to 3:1, most preferably 6:1 to 4:1, with a reaction temperature in the range of 75° to 160° C., most preferably 100° to 150° C.

In the reaction of converting a preformed N-oxyl compound to the N-hydrocarbyloxy derivative, the molar ratio of hydroperoxide:N-oxyl compound is preferably 10:1 to 2:1, most preferably 4:1 to 3:1, with a reaction temperature in the range of 75° to 160° C., most preferably 100° to 150° C.

The alkyl hydroperoxides which may be used in the process of this invention are tertiary-alkyl hydroperoxide, i.e., an alkane having a hydroperoxy group substituted on a tertiary carbon atom, or aralkyl hydroperoxides, wherein the hydroperoxy group is attached to the alpha-carbon of an aralkyl compound.

Suitable hydroperoxides are tert-butyl hydroperoxide, tert-amyl hydroperoxide, tert-hexyl hydroperoxide, tert-octyl hydroperoxide, ethylbenzene hydroperoxide, tetralin hydroperoxide or cumene (=isopropylbenzene) hydroperoxide.

Preferred hydroperoxides are tert-butyl hydroperoxide, tert-amyl hydroperoxide, ethylbenzene hydroperoxide, and cumene hydroperoxide. Expecially preferred are tert-butyl hydroperoxide and cumene hydroperoxide.

The reaction is conducted in the liquid phase in a hydrocarbon solvent. If the hydrocarbon solvent is low boiling (under 75° C.), the reaction can be carried out in a pressure vessel under pressure.

Illustrative of the hydrocarbon solvents suitable for use in the instant processes are the alkanes such as hexane, heptane, octane, nonane, decane, dodecane or octadecane; or the cycloalkanes such as cyclohexane, cyclooctane, cyclododecane, decalin, hexahydroindan, tetralin or methylcyclohexane; or the aromatic hydrocarbons such as toluene, ethylbenzene, xylene or isopropylbenzene (cumene); or the bicyclic or tricyclic saturated hydrocarbons such as norbornane, norcarnane or tricyclo [5.2,1.0$^{2,6}$]decane.

In most instances the solvent is used in amounts up to 20-30 moles of solvent per mole of amine or N-oxyl compound.

In the preferred procedure the amine or N-oxyl compound, the catalyst and the solvent are charged into a reaction vessel and the reaction mixture is maintained with agitation at the reaction temperature during the addition of peroxide. In another modification, reaction is effected continuously by contacting the amine or N-oxyl compound and the hydroperoxide in a solvent containing the catalyst.

Suitable reaction temperatures vary from 50° to 200° C., but preferably from 75° to 160° C.

The catalysts are selected from the group consisting of the metal carbonyls, the metal oxides, the metal acetylacetonates and the metal alkoxides where the metal is selected from the groups IVb, Vb, VIb, VIIb and VIII of the periodic table. Examples of effective catalysts include vanadium (III) acetylacetonate, vanadyl acetylacetonate, cobalt carbonyl, chromium (VI) oxide, titanium (IV) isopropoxide, titanium tetrabutoxide, molybdenum hexacarbonyl, molybdenum trioxide and the like.

Especially preferred are chromium trioxide and the molybdenum catalysts.

The reaction atmosphere can be ambient, oxygen enriched, or inert containing gases such as nitrogen, argon, and helium.

The amount of metal ion catalyst which is added to the reaction mixture is not narrowly critical and need only be added in amounts effective to initiate the reaction. An additional advantage of the instant process is that large amounts of catalyst are not required. The preferred range of catalyst is from 0.001 mole percent or lower to about 0.1 mole percent or higher based upon the hydroperoxide employed. This is preferably 0.01 to 0.3 mol of catalyst per mole of N—H or 0.01 to 0.2 mol of catalyst per mole of N-oxyl. Any amount can be used as long as it is catalytically effective. There is no limit to the upper range other than economic considerations.

Illustrative of the compounds which can be made by the instant process are the N-hydrocarbyloxy compounds listed below. It should be noted that in the case of the N-lower alkoxy derivatives the instant process must be run under pressure in order to keep the low boiling alkane solvent in liquid form during the reaction.

1-cyclohexyloxy-2,2,6,6-tetramethylpiperidin-4-yl benzoate, di-(1-nonyloxy-2,2,6,6-tetramethylpiperidin-4-yl) suberate, di-(1-cyclohexyloxy-2,2,6,6-tetramethylpiperidin-4-yl) phthlate, di-(1-cyclohexyloxy-2,2,6,6-tetramethylpiperidin-4-yl) sebacate, di-(1-cyclohexyloxy-2,2,6,6-tetramethylpiperidin-4-yl) isophthalate, alpha,alpha'-(di-1-benzyloxy-2,2,6,6-tetramethylpiperidin-4-yloxy)-p-xylene, di-(1-benzyloxy-2,2,6,6-tetramethylpiperidin-4-yl) sebacate, di-(1-benzyloxy-2,2,6,6-tetramethylpiperidin-4-yl) phthalate, di-(1-benzyloxy-2,2,6,6-tetramethylpiperidin-4-yl) isophthalate, di-(1-benzyloxy-2,2,6,6-tetramethylpiperidin-4-yl) diethylmalonate, di-[1-(alpha-methylbenzyloxy)-2,2,6,6-tetramethylpiperidin-4-yl] phthalate, di-[1-(alpha-methylbenzyloxy)-2,2,6,6-tetramethylpiperidin-4-yl] sebacate, di-(1-heptyloxy-2,2,6,6-tetramethylpiperidin-4-yl) sebacate, di-(1-alpha-methylbenzyloxy-2,2,6,6-tetramethylpiperidin-4-yl) terephthalate, di-(1-alpha-methylbenzyloxy-2,2,6,6-tetramethylpiperidin-4-yl) isophthalate, di-(1-cumyloxy-2,2,6,6-tetramethylpiperidin-4-yl) sebacate, 8-alpha-methylbenzyloxy-7,7,9,9-tetramethyl-8-aza-1,4-dioxaspiro[4.5]decane, 3,15-di-alpha-methylbenzyloxy-2,2,4,4,14,14,16,16-octamethyl-7,11,18,21-tetraoxa-3,15-diazatrispiro[5.2.2.5.2.2.]heneicosane, 3,15-dicyclohexyloxy-2,2,4,4,14,14,16,16-octamethyl-7,11,18,21-tetraoxa-3,15-diazatrispiro[5.2.2.5.2.2.]heneicosane, tris(1-cyclohexyloxy-2,2,6,6-tetramethylpiperidin-4-yl) trimellitate, tetra(1-cumyloxy-2,2,6,6-tetramethylpiperidin-4-yl) pyromellitate, di-(1-cyclohexyloxy-2,2,6,6-tetramethylpiperidin-4-yl) succinate, di-(1-alpha-methylbenzyloxy-2,2,6,6-tetramethylpiperidin-4-yl) succinate, di-(1-nonyloxy-2,2,6,6-tetramethylpiperidin-4-yl) sebacate, di-(1-octadecyloxy-2,2,6,6-tetramethylpiperidin-4-yl) sebacate, di-(1-cyclohexyloxy-2,2,6,6-tetramethylpiperidin-4-yl) terephthalate, 1-cyclohexyloxy-2,2,6,6-tetramethylpiperidin-4-yl 1-methoxy-2,2,6,6-tetramethylpiperidin-4-yl phthalate, di-(1-nonyloxy-2,2,6,6-tetramethylpiperidin-4-yl) succinate, di-(1-decyloxy-2,2,6,6-tetramethylpiperidin-4-yl) sebacate, di-(1-dodecyloxy-2,2,6,6-tetramethylpiperidin-4-yl) sebacate, 4-benzoyloxy-1-(1'-methylcyclohexyloxy)-2,2,6,6-tetramethylpiperidine, and di-[1-(1-methylcyclohexyloxy)-2,2,6,6-tetramethylpiperidin-4-yl] sebacate.

The instant N-hydrocarbyloxy derivatives are particularly effective in stabilizing organic materials against the degradative effects of actinic stimuli. Such organic materials include polyolefins, elastomers, polyvinyl chloride, polyesters and polyurethanes. They are particularly active as light stabilizers in ambient cured and acid catalyzed thermoset coatings or enamels. Since these materials are considerably less basic than conventional hindered amines, they do not inhibit or interfere with cure as is encountered with the conventional hindered amines. They likewise do not exhibit the color problems encountered with nitroxyl radicals and, in contrast to N-hydroxy derivatives, tend to resist air oxidation during handling. Finally, the N-hydrocarbyloxy hindered amines exhibit greater solubility in the solvents typically utilized in coatings. These areas are further described in copending U.S. application Ser. Nos. 099,411 and 099,420, both now abandoned.

The following examples will further illustrate the embodiments of this invention.

EXAMPLE 1

1-Cyclohexyloxy-2,2,6,6-piperidin-4-yl Benzoate

A mixture of 10.4 grams (39.8 mmol) of 2,2,6,6-piperidin-4-yl benzoate, 20.5 grams (159 mmol) of 70% aqueous tert-butyl hydroperoxide and 85 ml of cyclohexane is heated at reflux at 79° C. Water is collected in a Dean-Stark trap. The reaction mixture is cooled to 70° C. and molybdenum hexacarbonyl (0.52 gram, 2 mmol) is added. The reaction mixture is heated at reflux for twenty minutes, cooled to 75° C. and then treated with a second portion of molybdenum hexacarbonyl (0.53 gram, 2 mmol). The reaction mixture is heated at reflux for 24 hours. Suspended material is removed by filtration and the filtrate is concentrated to obtain a red oil. Flash chromatography (silica gel; 19:1 heptane:ethyl acetate) affords 10.7 grams of the title compound.

EXAMPLE 2

Di-(1-nonyloxy-2,2,6,6-tetramethylpiperidin-4-yl) Sebacate

A solution of 55 grams (427 mmol) of 70% aqueous tert-butyl hydroperoxide is added over 85 minutes to a mixture of 25 grams (52 mmol) of di-(2,2,6,6-tetramethylpiperidin-4-yl) sebacate, 1.5 grams (10.4 mmol) of molybdenum trioxide and 190 ml of a nonane fraction (b.p. 148°–156° C., Fluka) which mixture is first heated to 60° C. During the addition, the reaction temperature is slowly increased till the mixture begins to reflux. Water is collected in a Dean-Stark trap. The reaction mixture is heated at reflux for six hours after the addition of hydroperoxide is complete. The reaction mixture is then cooled to room temperature. The solids present are removed by filtration and washed with 25 ml of heptane. The filtrate is stirred for two hours with a solution of 26 grams of sodium sulfite in 500 ml of water. The resulting thick solution is diluted with ethyl acetate (300 ml) and 100 ml of water. The organic layer is separated, dried over anhydrous magnesium sulfate and concentrated to an oil. Flash chromatography (silica gel; 100:3 heptane:ethyl acetate) affords 26.6 grams (67% yield) of a colorless oil as the title compound.

Anal. Calcd. for $C_{46}H_{88}N_2O_6$: C, 72.2; H, 11.6; N, 3.7. Found: C, 72.5; H, 11.9; N, 3.6.

EXAMPLE 3

Di-(1-cyclohexyloxy-2,2,6,6-tetramethylpiperidin-4-yl) Phthalate

A mixture of 30.0 grams (67.5 mmol) of di-(2,2,6,6-tetramethylpiperidin-4-yl) phthalate, 27.5 grams (214 mmol) of 70% aqueous tert-butyl hydroperoxide, 2.0 grams of molybdenum trioxide and 200 ml of cyclohexane is heated to reflux at 81° C. Water is collected in a Dean-Stark trap. After 75 minutes, the reaction mixture is red. Another portion of tert-butyl hydroperoxide (42.5 grams of 70% aqueous solution, 330 mmol) is added over 30 minutes. After additional water is collected in the trap, the reaction mixture is transferred to a Fischer-Porter bottle and heated at 140° C. for 4.5 hours. The nearly colorless reaction mixture is treated with 6.9 grams (69 mmol) of 90% aqueous tert-butyl hydroperoxide and heated at 140° C. for 90 minutes to remove the last traces of pink color. The reaction mixture is cooled, filtered and stirred with a solution of 43 grams of sodium sulfite in 530 ml of water for 2 hours. Methylene chloride (600 ml) is added and the organic layer is separated, dried over anhydrous magnesium sulfate and concentrated to a crude solid. Purification (Waters Prep. 500A HPLC, 25:1 heptane:ethyl acetate) affords 31.0 grams (72% yield) of the title compound as a white solid, melting at 149°–151° C.

Anal. Calcd. for $C_{38}H_{60}N_2O_6$: C, 71.2; H, 9.4; N, 4.4. Found: C, 71.1; H, 9.3; N, 4.3.

EXAMPLE 4

Di-(1-cyclohexyloxy-2,2,6,6-tetramethylpiperidin-4-yl) Sebacate

A mixture of 20.0 g (41.6 mmol) of di-(2,2,6,6-tetramethylpiperidin-4-yl) sebacate, 43 g (334 mmol) of 70% aqueous t-butyl hydroperoxide, 1.3 g (9.0 mmol) of molybdenum trioxide, and 125 ml of cyclohexane is heated at reflux for 2.3 hours. Water is collected in a Dean-Stark trap. The red reaction mixture is cooled and transferred to a Fischer-Porter bottle. Fresh cyclohexane (25 ml) is used to thoroughly rinse the flask, and the rinsings are added to the pressure bottle. The pressure bottle is immersed in an oil bath (140° C.) for 3 hours whereupon the colorless reaction mixture is cooled to room temperature and filtered. The filtrate is stirred with 10 g of sodium sulfite in 90 ml of water for 2 hours to decompose unreacted hydroperoxide, then diluted with ethyl acetate (200 ml) and water (100 ml). The organic layer is washed with 10% sodium sulfite (100 ml), water (100 ml), saturated sodium chloride (100 ml), then dried over magnesium sulfate and concentrated at reduced pressure. The crude product is purified by flash chromatography (silica gel, 100:2 heptane:ethyl acetate) to afford 17.8 g (63% yield) of a white solid, m.p. 56°–9° C.

Anal. Calcd. for $C_4H_{72}N_2O_6$: C, 71.0; H, 10.7; N, 4.1. Found: C, 71.2; H, 10.7; N, 4.1.

EXAMPLE 5

Di-[1-(alpha-methylbenzyloxy)-2,2,6,6-tetramethylpiperidin-4-yl] Phthalate

The compound is prepared from 40.0 g of di-(1-oxyl-2,2,6,6-tetramethylpiperidin-4-yl) phthalate, 200 ml of ethylbenzene, and 2.0 g of molybdenum trioxide which are heated to 110° C. (nitrogen atmosphere). Thereafter, 65 g of 70% t-butyl hydroxperoxide in water is added dropwise over one hour. The reaction mixture is refluxed for 3 hours after the hydroperoxide addition is complete. The crude product is chromatographed on silica gel (9:1 hexane:ethyl acetate) to give 51.0 g (88% yield) of a soft glassy product.

Anal. Calcd. for $C_{42}H_{56}N_2O_6$: C, 73.7; H, 8.2; N, 4.1. Found: C, 74.1; H, 8.4; N, 4.1.

EXAMPLE 6

Di-[1-(alpha-methylbenzyloxy)-2,2,6,6-tetramethylpiperidine-4-yl] Sebacate

A mixture of 40.0 g (83 mmol) of di-(2,2,6,6-tetramethylpiperidin-4-yl) sebacate, 2.0 g of molybdenum trioxide, and 250 ml of ethylbenzene is heated to 110° C. (nitrogen atmosphere). A commercially available solution of 70% t-butyl hydroperoxide in water (64.3 g, 499 mmol) is added dropwise over 30 min. Water is collected in a Dean-Stark trap. Heating is continued for 90 minutes after the addition. The reaction mixture is filtered and evaporated. The resulting crude oil is dissolved in heptane (300 ml), and this solution is passed through a short column of silica gel. The first 350 ml of filtrate, nearly pure by TLC, is evaporated to give 41.7 g (70% yield) of the title compound, a viscous oil.

Anal. Calcd. for $C_{44}H_{68}N_2O_6$: C, 73.2; H, 9.5; N, 3.9. Found: C, 72.9; H, 9.7; N, 3.8.

EXAMPLE 7

Di-(1-heptyloxy-2,2,6,6-tetramethylpiperidin-4-yl) Sebacate

A mixture of 35.0 g (72.8 mmol) of di-(2,2,6,6-tetramethylpiperidin-4-yl) sebacate, 58.3 (582 mmol) of 90% aqueous t-butyl hydroperoxide, 2.0 g of molybdenum trioxide, and 250 ml of heptane is heated at 140° C. in a Fischer-Porter bottle. The pressure is maintained at 40-50 psi by occasional venting. Heating is discontinued after 7 hours. An additional portion (20.0 g) of 90% t-butyl hydroperoxide is added and the reaction mixture is heated for one hour at 140° C. The reaction is nearly colorless by this time. The reaction mixture is cooled and filtered to remove the catalyst. The organic phase is separated, dried over magnesium sulfate, and concentrated to 100 ml total volume. This solution is passed through silica gel with heptane as the eluent. The filtrate is evaporated to yield 36.9 g (72% yield) of the title compound, a nearly colorless oil.

Anal. Calcd. for $C_{42}H_{80}N_2O_6$: C 71.1; H 11.4; N 3.95. Found: C 71.3; H 11.8; N 3.9.

EXAMPLE 8

Di-(1-alpha-methylbenzyloxy-2,2,6,6-tetramethylpiperidin-4-yl) Terephthalate

A suspension of 40.0 g (90.0 mmol) of di-(2,2,6,6-tetramethylpiperidin-4-yl) terephthalate, 2.0 g of molybdenum trioxide, and 250 ml of ethylbenzene is heated to 110° C. t-Butyl hydroperoxide (70%, 69.5 g, 540 mmol) is rapidly added. No reaction is visible until water is removed by azeotropic distillation and the internal temperature reaches 115° C. Heating is continued for 6 hours. The nearly colorless reaction mixture is allowed to cool, then filtered and evaporated to yield a pink solid. The solid is recrystallized (9:1 2-propanol:methylene chloride) to yield 48.4 g of the title compound, a white solid, m.p. 150°–152° C. A second crop of 5.3 g is obtained from the mother liquor. Total yield 53.7 g (87% yield).

Anal. Calcd. for $C_{42}H_{56}N_2O_6$: C, 73.7; H, 8.2; N, 4.1. Found: C, 74.0; H, 8.2; N, 4.0.

EXAMPLE 9

Di-(1-alpha-methylbenzyloxy-2,2,6,6-tetramethylpiperidin-4-yl) Isophthalate a mixture of 40.0 g (90.0 mmol) of di-(2,2,6,6-tetramethylpiperidin-4-yl) isophthalate, 2.0 g of molybdenum trioxide, and 250 ml of ethylbenzene is heated to 110° C. t-Butyl hydroperoxide (70%, 69.5 g, 540 mmol) is added dropwise over a 45 min. period. The reaction mixture turns red during the addition. Water is removed by azeotropic distillation. The mixture is refluxed for 4 hours after the addition is complete. The catalyst is filtered, and the filtrate is evaporated to obtain a yellow oil. A Kugelrohr distillation (110° C., 0.1 mm Hg) is performed to remove volatile by-products. The residue, a viscous oil, is dissolved in hexane and passed through silica gel. Evaporation yields a crude solid which is recrystallized from ethanol to yield 39.8 g (65% yield) of the title compound, a white powder, m.p. 118°–34° C.

Anal. Calcd. for $C_{42}H_{56}N_2O_6$: C, 73.7; H, 8.2; N, 4.1. Found: C, 73.4; H, 8.3; N, 4.1.

EXAMPLE 10

8-alpha-Methylbenzyloxy-7,7,9,9-tetramethyl-8-aza-1,4-dioxaspiro[4.5]decane

A mixture of 38.1 g (191 mmol) of 7,7,9,9-tetramethyl-8-aza-1,4-dioxaspiro[4.5]decane, 73.8 g (574 mmol) of 70% aq. t-butyl hydroperoxide, 2.0 g of molybdenum trioxide, and 130 ml of ethylbenzene is refluxed for 6 hours. Water is collected in a Dean-Stark trap. The catalyst is filtered and the filtrate is concentrated at reduced pressure. The residue is dissolved in heptane and passed through silica gel. A Kugelrohr distillation (120° C., 0.1 mm Hg) is used to remove volatile by-products. The title compound crystallizes on standing.

Anal. Calcd. for $C_{19}H_{29}NO_3$: C, 71.4; H, 9.1; N, 4.4. Found: C, 70.3; H, 9.2; N, 4.4.

EXAMPLE 11

3,15-Di-alpha-methylbenzyloxy-2,2,4,4,14,14,16,16-octamethyl-7,11,18,21-tetraoxa-3,15-diazatrispiro[5.2.2.5.2.2.]heneicosane The title compound is prepared from 2,2,4,4,14,14,16,16-octamethyl-7,11,18,21-tetraoxa-3,15-diazatrispiro[5.2.2.5.2.2]heneicosane according to the procedure given in Example 10. The catalyst is filtered and the filtrate is concentrated to yield an oil which is crystallized from ethanol to give 19.6 g (65% yield) of a white powder, m.p. 150°–53° C.

EXAMPLE 12

3,15-Dicyclohexyloxy-2,2,4,4,14,14,16,16-octamethyl-7,11,18,21-tetraoxa-3,15-diazatrispiro[5.2.2.5.2.2.-]heneicosane A mixture of 16.7 g (37.9 mmol) of 3,15-dioxyl-2,2,4,4,14,14,16,16-octamethyl-7,11,18,21-tetraoxa-3,15-diazatrispiro[5.2.2.5.2.2.]heneicosane, 22.8 g (227 mmol) of 90% aq. t-butyl hydroperoxide, 2.0 g of molybdenum trioxide, and 125 ml of cyclohexane is heated in a Fischer-Porter bottle at 155°–160° C. (bath temperature) for 6 hours. The pressure is maintained at 40–50 psi by occasional venting. The catalyst is filtered and the filtrate is concentrated. The residue is dissolved in hexane and passed through silica gel. Crystallization from 2-propanol yields 8.0 g (35%) of a white solid, m.p. 163°–175° C.

Anal. Calcd. for $C_{35}H_{62}N_2O_6$: C, 69.3; H, 10.3; N, 4.6. Found: C, 68.7; H, 10.3; N, 4.7.

EXAMPLE 13

4-Benzoyloxy-1-cumyloxy-2,2,6,6-tetramethylpiperidine

A mixture of 10.1 g (38.6 mmol) of 4-benzoyloxy-2,2,6,6-tetramethylpiperidine, 15.6 g (155 mmol) of 90% aqueous tert-butyl hydroperoxide, 600 mg of molybdenum trioxide and 60 ml of cumene is heated at 95° C. for two hours. The catalyst is removed by filtration and the filtrate is then evaporated at reduced pressure. The residual red oil is chromatographed on silica gel to afford 5.8 g (38% yield) of a white powder, m.p. 105°–108° C.

Anal. Calcd. for $C_{25}H_{33}NO_3$: C, 75.9; H, 8.4; N, 3.5. Found: C, 75.7; H, 8.4; N, 3.5.

EXAMPLE 14

Di-(1-cyclohexyloxy-2,2,6,6-tetramethylpiperidin-4-yl) Succinate

A two-phase mixture of 70% aqueous t-butyl hydroperoxide (103.9 g, 807 mmol), cyclohexane (200 ml) and sodium chloride (15 g) is shaken in a separatory funnel. The organic phase is dried over magnesium sulfate, filtered, and added to 40.0 g (101 mmol) of di-(2,2,6,6-tetramethylpiperidin-4-yl) succinate. Molybdenum trioxide (2.0 g) is added, and the mixture is refluxed for one hour. Water is collected in a Dean-Stark trap. The entire reaction mixture is then transferred to a Fischer-Porter bottle and heated at 140° C. for 6 hours. Additional t-butyl hydroperoxide (90%, 10.1 g, 101 mmol) is added and heating is resumed for another 4 hours. The colorless reaction mixture is filtered, concentrated, and dissolved in heptane (200 ml). The heptane solution is passed through a short column of silica gel with heptane. Subsequent evaporation affords an oil which is crystallized from ethanol to yield 41.2 g (69%) of a white powder, m.p. 122°–6° C.

Anal. Calcd. for $C_{34}H_{60}N_2O_6$: C, 68.9; H, 10.2; N, 4.7. Found: C, 68.4; H, 10.5; N, 4.5.

EXAMPLE 15

Di-(1-alpha-methylbenzyloxy-2,2,6,6-tetramethyl-piperidin-4-yl) Succinate

The title compound is prepared following the procedure given in Example 6 utilizing the succinate starting material. Crystallization from ethanol affords a 78% yield of a white solid, mp 85°–88° C.

Anal. Calcd. for $C_{38}H_{56}N_2O_6$: C, 71.7; H, 8.9; N, 4.4. Found: C, 71.5; H, 8.6; N, 4.3.

EXAMPLE 16

Di-(1-nonyloxy-2,2,6,6-tetramethylpiperidin-4-yl) Suberate

The title compound is prepared following the procedure given in Example 14 using the suberate starting material and nonane, except that the reaction mixture is refluxed for 22 hours at atmospheric pressure. The crude product is passed through a short column of silica gel with heptane as the eluent to obtain a colorless oil.

EXAMPLE 17

Di-(1-octadecyloxy-2,2,6,6-tetramethylpiperidin-4-yl) Sebacate

The reaction is run in a Fischer-Porter bottle in a nitrogen atmosphere. The reaction vessel is charged with 15.0 g (31.2 mmol) of di-(2,2,6,6-tetramethylpiperidin-4-yl) sebacate, 101 g of octadecane, 25.3 g (253 mmol) of 90% t-butyl hydroperoxide, and 1.25 g of molybdenum trioxide. The Fischer-Porter bottle is placed in an oil bath and the bath temperature is brought to 143° C. over 1.3 hours. Heating is continued another 3.2 hours at 145°±3° C. The colorless reaction mixture is cooled to room temperature, diluted with hexane (100 ml), and filtered to remove solids. The solids are rinsed with hexane (2×50 ml). The organic solution is stirred for 90 minutes with 16.1 g sodium sulfite in 200 ml of water to decompose unreacted hydroperoxide. Ethyl acetate is added (200 ml), and the organic solution is washed with water (4×250 ml), dried over magnesium sulfate, and concentrated to obtain 121 g of a colorless oil. The crude material is purified by flash chromatography (silica gel; heptane; then 20:1 heptane:ethyl acetate) to afford 20.8 g (66% yield) of the title compound as a colorless oil.

Anal. Calcd. for $C_{64}H_{124}N_2O_6$: C, 75.5; H, 12.3; N, 2.75. Found: C, 75.1; H, 12.6; N, 3.2.

EXAMPLE 18

Di-(1-cyclohexyloxy-2,2,6,6-tetramethylpiperidin-4-yl) Isophthalate

A mixture of 35.0 g (78.7 mmol) of di-(2,2,6,6-tetramethyl-piperidin-4-yl) isophthalate, 47.3 g (472 mmol) of 90% aqueous t-butyl hydroperoxide, 2.0 g of molybdenum trioxide, and 300 ml of cyclohexane is heated two hours at 140° C. in a Fischer-Porter bottle. The red reaction mixture is treated with an additional 20.0 g (90%, 200 mmol) of t-butyl hydroperoxide and heated at 140° C. for 120 minutes to discharge the red color. The reaction mixture is cooled, filtered, and the filtrate is evaporated to an oil which is crystallized from ethanol to afford 36.2 g (72% yield) of a white solid, m.p. 135°–141° C.

Anal. Calcd. for $C_{38}H_{60}N_2O_6$: C, 71.2; H, 9.4; N, 4.4. Found: C, 71.1; H, 9.6; N, 4.3.

EXAMPLE 19

Di-(1-nonyloxy-2,2,6,6-tetramethylpiperidin-4-yl) Succinate

The title compound, a light yellow oil, is prepared from di-(2,2,6,6-tetramethylpiperidin-4-yl) succinate and nonane according to the procedure given in Example 16.

Anal. Calcd. for $C_{46}H_{76}N_2O_6$: C, 70.5; H, 11.2; N, 4.1. Found: C, 70.6; H, 11.3; N, 4.0.

EXAMPLE 20

Di-(1-decyloxy-2,2,6,6-tetramethylpiperidin-4-yl) Sebacate t-Butyl hydroperoxide (55.0 g of a 70% aqueous solution, 427 mmol) is added dropwise over 15 minutes to a mixture of 25.0 g (52.0 mmol) of di-(2,2,6,6-tetramethylpiperidin-4-yl) sebacate, 1.5 g (10.4 mmol) of molybdenum trioxide, and 225 ml of n-decane which has been heated to 90° C. The reaction mixture is refluxed for 7.5 hours, and water is collected in a Dean-Stark trap. The reaction mixture is cooled to room temperature, and then stirred for 2 hours with a solution of 26 g of sodium sulfite in 500 ml of water. The reaction mixture is diluted with ethyl acetate (200 ml). The organic layer is dried over magnesium sulfate and concentrated to an oil. The crude product is purified by flash chromatography (silica gel; 97:3 heptane:ethyl acetate) to afford 29.2 g (71% yield) of the title compound, as a colorless oil.

Anal. Calcd. for $C_{48}H_{92}N_2O_6$: C, 72.7; H, 11.7; N, 3.5. Found: C, 73.1; H, 12.2; N, 3.5.

EXAMPLE 21

Di-(1-dodecyloxy-2,2,6,6-tetramethylpiperidin-4-yl) Sebacate

The title compound, a colorless oil, is prepared from di-(2,2,6,6-tetramethylpiperidin-4-yl) sebacate and n-dodecane according to the procedure given in Example 20.

Anal. Calcd. for $C_{52}H_{100}N_2O_6$: C, 73.5; H, 11.9; N, 3.3. Found: C, 73.2; H, 12.2; N, 3.2.

EXAMPLE 22

4-Benzoyloxy-1-(1'-methylcyclohexyloxy)-2,2,6,6-tetramethylpiperidine t-Butyl hydroperoxide (70%, 65.2 g, 507 mmol), methylcyclohexane (150 ml), and sodium chloride (10 g) are agitated in a separatory funnel. The organic layer is dried over magnesium sulfate. The t-butyl hydroperoxidemethylcyclohexane solution is mixed with 35.0 g (127 mmol) of 4-benzoyloxy-1-oxyl-2,2,6,6-tetramethylpiperidine, 2.0 g of molybdenum trioxide, and 50 ml of methylcyclohexane. The reaction mixture is heated at reflux for 5 hours, then cooled to room temperature, filtered, and concentrated at reduced pressure. The crude product is diluted with heptane and passed through a short column of silica gel with heptane as the eluent to afford, after evaporation of solvent, 42.4 g (89% yield) of a clear colorless oil.

Anal. Calcd. for $C_{23}H_{35}NO_3$: C, 74.0; H, 9.4; N, 3.7. Found: C, 74.3; H, 9.8; N, 3.7.

EXAMPLE 23

Di-[1-(1-Methylcyclohexyloxy)-2,2,6,6-tetramethylpiperidin-4-yl] Sebacate t-Butyl hydroperoxide (70%, 133.9 g, 1.04 mol), methylcyclohexane (250 ml), and sodium chloride (20 g) are agitated in a separatory funnel. The organic layer is dried over magnesium sulfate. The t-butyl hydroperoxidemethylcyclohexane solution is mixed with 50.0 g (104 mmol) of di-(2,2,6,6-tetramethylpiperidin-4-yl) sebacate, 3.0 g of molybdenum trioxide, and 100 ml of methylcyclohexane. The reaction mixture is heated at reflux for 4.5 hours and water is collected in a Dean-Stark trap. The reaction is cooled to room temperature and filtered. The filtrate is concentrated at reduced pressure to obtain an oil which is purified by flash chromatography (silica gel; 19:1 heptane:ethyl acetate) to obtain 51.6 g (72% yield) of a colorless oil.

Anal. Calcd. for $C_{42}H_{76}N_2O_6$: C, 71.6; H, 10.9; N, 4.0. Found: C, 71.4; H, 11.0; N, 3.9.

EXAMPLE 24

4-Acetamido-1-cyclohexyloxy-2,2,6,6-tetramethylpiperidine

A stirred mixture of 10.0 g of 4-acetamido-2,2,6,6-tetramethylpiperidine-1-oxyl, 16 ml of 70% aqueous tert-butylhydroperoxide and 0.67 g of molybdenum trioxide in 75 ml of cyclohexane is heated under reflux in a flask fitted with a Dean-Stark apparatus. After 6 ml of water is collected, the reaction mixture is transferred to a Fisher Porter apparatus and heated at 140° C. and 30 psi for 4 hours. The decolorized reaction mixture is filtered and the filtrate is washed with water, aqueous sodium sulfite, brine, dried (MgSO$_4$) and concentrated to give 13.61 g of a white solid. Recrystallization from heptane affords 10.39 g of the title compound as a white crystalline solid, m.p. 140°–44° C.

Anal. Calcd. for $C_{17}H_{32}N_2O_2$: C, 68.9; H, 10.9; N, 9.5. Found: C, 68.6; H, 11.3; N, 9.3.

EXAMPLE 25

To show the criticality of using a metal catalyst, preferably a molybdenum catalyst, in the instant process, 1-oxyl-2,2,6,6-tetramethylpiperidin-4-yl benzoate (39.8 mmol) and 99.5 mmol (2.5 molar equivalents) of 70% aqueous tert-butyl hydroperoxide are dissolved in 85 ml of cyclohexane. The solution is refluxed at 80° C. and water is collected in a Dean-Stark trap. The reaction mixture is then heated for 24 hours at 80° C. The materials present in the reaction mixture at the end of this reaction period are isolated by flash chromatography.

The same experiment is then repeated except that 4 mmol (0.1 molar equivalent) of molybdenum hexacarbonyl or of molybdenum trioxide catalyst is also added to the reaction mixture before reaction begins.

The results of these experiments are given below.

| Catalyst | % N-oxyl compound recovered after 24 hours | % Yield of N-cyclohexyloxy product |
|---|---|---|
| none | 79 | 14 |
| molybdenum hexacarbonyl | 24 | 62 |
| molybdenum trioxide | 2 | 93 |

It is clear from these data that the presence of the molybdenum catalyst makes a tremendous difference in the rate of reaction and in the yield and purity of the desired N-hydrocarbyloxy product obtained.

EXAMPLE 26

To show that the oxidation of the hindered amine N—H to the corresponding N-oxyl compound occurs much more rapidly than the subsequent conversion of the N-oxyl compound to the final N-hydrocarbyloxy derivative, a mixture of 20.5 grams (159 mmol) of 70% aqueous tert-butyl hydroperoxide, 50 ml of cyclohexane and 2 grams of sodium chloride is agitated in a separatory funnel. The organic layer is dried over anhydrous magnesium sulfate and then rapidly added to a refluxing mixture of 10.4 grams (39.8 mmol) of 2,2,6,6-tetramethylpiperidin-4-yl benzoate, 0.6 grams (4.2 mmol) of molybdenum trioxide, 40 ml of cyclohexane and 10 grams of chlorobenzene. The chlorobenzene is an inert solvent used as an internal standard for vapor phase chromatography measurements used to identify the reaction results given in the table below.

The reaction mixture is heated at reflux (78°–82° C.) for 8 hours. Water is collected in a Dean-Stark trap. Small aliquots are withdrawn from the reaction mixture and analyzed by vapor phase chromatography. Components in the reaction mixture are identified by comparing retention times with those of authentic samples.

Four molar equivalents of tert-butyl hydroperoxide are used per mole of amine in carrying out this reaction.

| Analysis of Reaction Mixture by Vapor Phase Chromatography | | | |
|---|---|---|---|
| Time (minutes) | % N-H compound | % N-oxyl compound | % N-cyclohexyloxy compound |
| 0.5* | 43.0 | 3.5 | — |
| 5 | 10.3 | 41.1 | — |
| 10 | 0 | 53.7 | — |
| 15 | 0 | 35.0 | 1.9 |
| 30 | 0 | 36.8 | 11.0 |
| 60 | 0 | 30.1 | 24.2 |
| 120 | 0 | 15.8 | 28.6 |
| 240 | 0 | 8.4 | 45.5 |
| 480 | 0 | 2.6 | 65.7 |

*the first sample is withdrawn after the hydroperoxide addition is complete at 30 seconds These data show that oxidation of the hindered amine N—H to the corresponding N-oxyl compound occurs rapidly within the first 5 to 10 minutes. At that point no trace of amine N—H remains and a high conversion to N-oxyl compound is observed.

The subsequent conversion of N-oxyl compound to the N-cyclohexyloxy derivative takes much longer. More than two hours is required before the N-hydrocarbyloxy compound is the predominant product. After 8 hours, a good yield of the desired N-hydrocarbyloxy compound is observed with very little N-oxyl intermediate still present.

EXAMPLE 27

To show that there must be sufficient hydroperoxide remaining after the amine N—H is converted to the N-oxyl intermediate for the second step of converting the N-oxyl to the corresponding N-hydrocarbyloxy product to occur, the procedure described in Example 26 is repeated except that only two molar equivalents of hydroperoxide are used per mole of amine. The reaction time is extended to 24 hours at reflux temperature of cyclohexane (78°–82° C.).

| Analysis of Reaction Mixture by Vapor Phase Chromatography | | | |
|---|---|---|---|
| Time (minutes) | % N-H compound | % N-oxyl compound | % N-cyclohexyloxy compound |
| 0.5* | 46.4 | 5.3 | — |
| 5 | 21.9 | 32.4 | — |
| 10 | 10.3 | 43.8 | — |
| 15 | 2.3 | 35.0 | — |
| 30 | 0.3 | 50.5 | 1.1 |
| 60 | 0 | 57.2 | 5.5 |
| 120 | 0 | 51.5 | 10.6 |
| 180 | 0 | 52.7 | 14.8 |
| 420 | 0 | 54.2 | 22.3 |
| 1440 | 0 | 53.5 | 22.2 |

*the first sample is withdrawn after the hydroperoxide addition is complete at 30 seconds These data show that, when there is not sufficient hydroperoxide remaining after the oxidation of the amine N—H to the corresponding N-oxyl compound has occurred, the subsequent conversion of N-oxyl to the N-hydrocarbyl product is inhibited and does not go to completion as it does in Example 26 where adequate hydroperoxide is present throughout the entire reaction period.

EXAMPLE 28

1-(1,2,3,4-Tetrahydronaphthenyloxy)-2,2,6,6-tetramethylpiperidin-4-yl Benzoate

When an equivalent amount of 1,2,3,4-tetrahydronaphthalene (tetralin) is substituted for methylcyclohexane in Example 22, the above-named compound is obtained.

EXAMPLE 29

Bis(1-decahydronaphthalenyloxy-2,2,6,6-tetramethylpiperidin-4-yl) Sebacate

A mixture of 25.0 g (0.052 mol) of bis(2,2,6,6-tetramethylpiperdin-4-yl) sebacate, 55.0 g (0.427 mol) of 70% aqueous tert-butyl hydroperoxide, 1.5 g (0.01 mol) of molybdenum trioxide and 180 ml of decahydronaphthalene (decalin) is heated at reflux for 4.5 hours till the red color disappears. Water is collected in a Dean-Stark trap. The molybdenum trioxide is removed by filtration and the filtrate is stirred with a solution of 26 g of sodium sulfite in 500 ml of water to decompose unreacted tert-butyl hydroperoxide. The 2-phase mixture is diluted with 200 ml of ethyl acetate. The organic layer is washed with saturated sodium chloride solution, dried over anhydrous magnesium sulfate and concentrated at reduced pressure to give an oil. Purification by flash chromatography (silica gel, 19:1 heptane:ethyl acetate) affords 28.8 g (71% yield) of the title compound as a pale yellow oil.

Anal. Calcd. for $C_{48}H_{84}N_2O_6$: C, 73.4; H, 10.8; N, 3.6. Found: C, 74.9; H, 11.5; N, 3.4.

EXAMPLE 30

Bis(1-heptyloxy-2,2,6,6-tetramethylpiperidin-4-yl) Succinate

70% Aqueous tert-butyl hydroperoxide (78.9 g, 0.613 mol) is added over a 30-minute period to a mixture of 55.0 g (0.1 39 mol) of bis(2,2,6,6-tetramethylpiperidin-4-yl) succinate, 1.0 g of molybdenum trioxide and 400 ml of n-heptane which has been heated to 110° C. Water is collected in a Dean-Stark trap. After addition is complete, the reaction mixture is heated at reflux for 30 minutes. Another portion of 70% aqueous tert-butyl hydroperoxide (100 g, 0.777 mol) is added to the red reaction mixture over a 90-minute period. The reaction is heated at reflux for an additional 16 hours to discharge the red color. The molybdenum trioxide is removed by filtration, and the filtrate is evaporated at reduced pressure. The residue is purified by flash chromatography (19:1, then 9:1 heptane: ethyl acetate) on silica gel to afford 63.6 g (73% yield) of the title compound as a clear yellow liquid.

Anal. Calcd. for $C_{36}H_{68}N_2O_6$: C, 69.2; H, 11.0; N, 4.5. Found: C, 68.8; H, 11.1; N, 4.5.

EXAMPLE 31

Bis(1-octyloxy-2,2,6,6-tetramethylpiperidin-4-yl) Sebacate

70% Aqueous tert-butyl hydroperoxide (140 g, 1.09 mol) is added over a 6-hour period to a mixture of 75.4 g (0.157 mol) of bis(2,2,6,6-tetramethylpiperidin-4-yl) sebacate, 1.25 g (8.7 mmol) of molybdenum trioxide and 570 ml of n-octane, that is first heated to 115° C., under a nitrogen atmosphere. During the addition, the reaction mixture is maintained at reflux. Water is collected in a Dean-Stark trap. Upon completion of the addition, the red reaction mixture is heated at reflux (95°–97° C.) for seven hours to discharge the red color. The molybdenum trioxide is removed by filtration. The yellow filtrate is stirred at ambient temperature for 30 minutes with 15 g of activated charcoal (DARCO) to remove some of the yellow color before being concentrated under reduced pressure. The crude product is purified by flash chromatography on silica gel (100:3 heptane:ethyl acetate) to afford 92.9 g (80% yield) of the title compound as a colorless oil.

Anal. Calcd. for $C_{44}H_{84}N_2O_6$: C, 71.7; H, 11.5; N, 3.8. Found: C, 71.6; H, 11.5; N, 3.6.

EXAMPLE 32

Di-(1-norbornyloxy-2,2,6,6-tetramethylpiperidin-4-yl) Sebacate

When using the general procedure of Example 17 an equivalent amount of norbornane is substituted for octadecane, the above-named compound is obtained.

EXAMPLE 33

Bis-(1-tricyclo[5.2.1.0$^{2,6}$]decyloxy-2,2,6,6-tetramethylpiperidin-4-yl) Sebacate When using the general procedure of Example 17 an equivalent amount of tricyclo[5.2.1.0$^{2,6}$]decane is substituted for octadecane, the above-named compound is obtained.

EXAMPLE 34

Bis-(1-nonyloxy-2,2,6,6-tetramethylpiperidin-4-yl) Sebacate

A 2-phase mixture of 85.7 g (0.666 mol) of 70% aqueous tert-butyl hydroperoxide, 150 ml of n-nonane and 10 g of sodium chloride is agitated in a separatory funnel. The organic layer is dried over anhydrous magnesium sulfate. The magnesium sulfate is removed by filtration and then washed rinsed with 50 ml of n-nonane. The nonane rinse solution is then added to the original filtrate. A mixture of 40.0 g (0.083 mol) of bis-(2,2,6,6-tetramethylpiperidin-4-yl) sebacate, the combined hydroperoxide-nonane solution and an additional 50 ml of nonane is heated at reflux in a nitrogen atmosphere for 18 hours. The reaction mixture is still red at the end of this period. The nonane solvent is evaporated under reduced pressure and the residue is purified by chromatography (Waters Prep 500A HPLC, 29:1, heptane:ethyl acetate) to obtain 17.2 g (27% yield) of the title compound as a clear, colorless oil.

The yield of the desired compound is only 27% even though the reaction is run for 18 hours. The effect of the absence of molybdenum catalyst in this reaction is evident since there is still some N-oxyl intermediate present at the end of the 18-hour reaction time. This is in contrast to Example 2 where the same compound is made in the presence of molybdenum trioxide catalyst with a yield of desired product of 67% being obtained after only 7.5 hours reaction.

EXAMPLE 35

Bis-(1-alpha-methylbenzyloxy-2,2,6,6-tetramethyl-piperidin-4-yl) Sebacate

A solution of 80% cumene hydroperoxide (107 g, 0.562 mol) in cumene is steam distilled to remove cumene. The wet cumene hydroperoxide is saturated with sodium chloride (20 g), extracted with 120 ml of ethylbenzene and dried over magnesium sulfate. The solution of cumene hydroperoxide in ethylbenzene is added over 2.25 hours to a mixture of 30.0 g (0.0624 mol) of bis-(2,2,6,6-tetramethylpiperidin-4-yl) sebacate, 1.0 g of molybdenum trioxide and 80 ml of ethylbenzene which is first heated to 110° C. under a nitrogen atmosphere. The reaction mixture becomes red after 30 minutes. After the addition is complete, the reaction mixture is heated at reflux (136° C.) for 5 hours till the red color is no longer observed. Molybdenum trioxide is removed by filtration. The filtrate is concentrated under reduced pressure. The crude product is dissolved in heptane (150 ml) and passed through a short column of silica gel to obtain 23.8 g (53% yield) of the title compound as a cloudy, pale yellow syrup.

In the presence of the molybdenum trioxide catalyst, this reaction went to completion at 136° C. in about 7 hours to give the desired product in 53% yield.

EXAMPLE 36

Bis-(1-alpha-methylbenzyloxy-2,2,6,6-tetramethyl-piperidin-4-yl) Sebacate

The reaction described in Example 35 is repeated except that no molybdenum trioxide catalyst is used. A reaction mixture of 30.0 g (0.0624 mol) of bis-(2,2,6,6-tetramethylpiperidin-4-yl) sebacate, 85.6 g (0.562 mol) of cumene hydroperoxide and 200 ml of ethylbenzene is heated for 23 hours at 130° C. under a nitrogen atmosphere. The ethylbenzene solvent is evaporated under reduced pressure, and the crude product is purified by flash chromatography (silica gel; 19:1 heptane:ethyl acetate) to afford 26.4 g (59% yield) of the title compound as a pale yellow syrup.

At essentially the same temperature, but with no molybdenum trioxide catalyst present, it took over three times as long for the reaction to go to completion. The final yield of product is essentially the same as that observed in Example 35 using the molybdenum trioxide catalyst.

When the above-described experiment is repeated, but the reaction temperature kept at only 110° C., the yield of final product is only 31%.

EXAMPLE 37

Bis-(1-heptyloxy-2,2,6,6-tetramethylpiperidin-4-yl) Sebacate

A solution of 80% cumene hydroperoxide in cumene (107 g, 0.562 mol) is steam distilled to remove the cumene. The wet hydroperoxide is saturated with sodium chloride (15 g) and extracted with 200 ml of n-heptane. The solution of cumene hydroperoxide in heptane is dried over anhydrous magnesium sulfate and then added to a mixture of 30.0 g (0.0624 mol) of bis-(2,2,6,6-tetramethylpiperidin-4-yl) sebacate and 0.5 g of molybdenum trioxide. The reaction mixture is heated at reflux (98° C.) for 20 hours under a nitrogen atmosphere. Heptane is removed under reduced pressure. The red residue is dissolved in heptane (100 ml) and passed through a short column of silica gel with additional heptane. The red filtrate is concentrated to obtain 20.3 g of an oil which is a mixture of several different compounds. Comparison with an authentic sample of the title compound by thin layer chromatography reveals that the product mixture contains only a trace of the title compound.

EXAMPLE 38

Bis-(1-alpha-methylbenzyloxy-2,2,6,6-tetramethylpiperidin-4-yl) Sebacate

A 2-phase mixture of 85.7 g (0.666 mol) of 70% aqueous tert-butyl hydroperoxide, 250 ml of ethylbenzene and 10 g of sodium chloride is agitated in a separatory funnel. The organic layer is dried over anhydrous magnesium sulfate. A mixture of 40.0 g (0.0832 mol) of bis-(2,2,6,6-tetramethylpiperidin-4-yl) sebacate and the tert-butyl hydroperoxideethylbenzene solution is heated to reflux (136° C.) under a nitrogen atmosphere. To this mixture is added over a 5-minute period, a solution of 5.0 g of titanium tetrabutoxide in 35 ml of ethylbenzene. The reaction mixture becomes red and water is collected in a Dean-Stark trap. The reaction mixture is heated at reflux for 18 hours. The red color remains. The solids are then removed by filtration, and the filtrate is concentrated under reduced pressure to give a red oil. The oil is dissolved in heptane (100 ml) and passed through a short column of silica gel with additional heptane. Further purification (Waters Prep 500A HPLC; 29:1 heptane:ethyl acetate) affords 4.0 g (7% yield) of the title compound as a cloudy, colorless syrup.

EXAMPLE 39

Bis-(1-nonyloxy-2,2,6,6-tetramethylpiperidin-4-yl) Sebacate

A 2-phase mixture of 85.7 g (0.666 mol) of 70% aqueous tert-butyl hydroperoxide, 200 ml of n-nonane and 15 g of sodium chloride is agitated in a separatory funnel. The organic layer is dried over anhydrous magnesium sulfate. A mixture of 40.0 g (0.0832 mol) of bis-(2,2,6,6-tetramethylpiperidin-4-yl) sebacate and the tert-butyl hydroperoxidenonane solution is heated to reflux (151° C.) under a nitrogen atmosphere. To this mixture is added over a 10-minute period, a solution of 5.0 g of titanium tetrabutoxide in 50 ml of nonane. The reaction mixture turns red. Water is collected in a Dean Stark trap. The reaction mixture is heated at reflux for 17 hours. Another 5.0 g of titanium tetrabutoxide is added, and the reaction mixture is heated at reflux for an additional 7 hours. Solids are removed by filtration, and the filtrate is concentrated under reduced pressure. The crude red oil obtained is purified by chromatography (Waters Prep 500A HPLC; 29:1 heptane:ethyl acetate) to give 3.6 g (6% yield) or the title compound as a light yellow oil.

EXAMPLE 40

Bis-(1-nonyloxy-2,2,6,6-tetramethylpiperidin-4-yl) Sebacate

A 2-phase mixture of 85.7 g (0.666 mol) of 70% aqueous tert-butyl hydroperoxide, 200 ml of n-nonane and 10 g of sodium chloride is agitated in a separatory funnel. The organic layer is dried over anhydrous magnesium sulfate. A mixture of 40.0 g (0.0832 mol) of bis-(2,2,6,6-tetramethylpiperidin-4-yl) sebacate and the tert-butyl hydroperoxide solution in n-nonane is heated to reflux (151° C.) under a nitrogen atmosphere. Vanadium (III) acetylacetonate (2.0 g) is added over a 15-minute interval. The reaction mixture is diluted with 50 ml of nonane. The reaction mixture is heated at reflux for 22 hours. Water is collected in a Dean-Stark trap. The mixture turns red and then darkens in color. The solvent is then removed under reduced pressure. The residue is dissolved in 150 ml of heptane and then passed through a short column of silica gel with additional heptane. The crude product is purified by chromatography (Waters Prep 500A HPLC; 29:1 heptane:ethyl acetate) to afford 2.5 g (4% yield) of the title compound.

EXAMPLE 41

Bis-(1-alpha-methylbenzyloxy-2,2,6,6-tetramethylpiperidin-4-yl) Sebacate

A 2-phase mixture of 85.7 g (0.666 mol) of 70% aqueous tert-butyl hydroperoxide, 200 ml of ethylbenzene and 10 g of sodium chloride is agitated in a separatory funnel. The organic layer is dried over anhydrous magnesium sulfate. A mixture of 40.0 g (0.0832 mol) of bis-(2,2,6,6-tetramethylpiperidin-4-yl) sebacate and the tert-butyl hydroperoxideethylbenzene solution is heated to 110° C. under a nitrogen atmosphere. To this mixture is added 4.0 g of vanadium (III) acetylacetonate over a 20-minute period. The reaction mixture is diluted with 50 ml of ethylbenzene. The reaction mixture is heated at reflux (136° C.) for five hours. Water is collected in a Dean-Stark trap. The reaction mixture first turns bright red and eventually deep blue. The blue solution is concentrated at reduced pressure. The residue is dissolved in heptane (100 ml) and then passed through a short column of silica gel with additional heptane as the eluent. The crude product is then purified by chromatography (Waters Prep 500A HPLC; 29:1 heptane:ethyl acetate) to afford 39.2 g (65% yield) of a yellow oil. The nmr spectrum of this product shows it to be identical to that of an authentic sample of the title compound.

EXAMPLE 42

Di-(1-cyclododecyloxy-2,2,6,6-tetramethylpiperidin-4-yl) Sebacate

A mixture of 30.1 g (62.6 mmol) of di-(2,2,6,6-tetramethylpiperidin-4-yl) sebacate, 44 g (439 mmol) of 90% aqueous tert-butyl hydroperoxide, 0.5 g of molybdenum trioxide and 207 g of cyclododecane is heated in a Fischer-Porter pressure bottle at 135°–145° C. for 7.5 hours. The reaction mixture is purified first by flash chromatography (silica gel, heptane, then 20:1 heptane:ethyl acetate) and then by HPLC (Waters Prep 500A, 25:1 hexane:ethyl acetate) to afford 36.3 g (69% yield) of the title compound, a white solid, m.p. 70°–78° C.

Anal. Calcd. for $C_{52}H_{96}N_2O_6$: C, 73.9; H, 11.5; N, 3.3. Found: C, 74.1; H, 11.5; N, 3.1.

EXAMPLE 43

Di-(1-cyclooctyloxy-2,2,6,6-tetramethylpiperidin-4-yl) Sebacate

A mixture of 75 g (156 mmol) of di-(2,2,6,6-tetramethylpiperidin-4-yl) sebacate, 1.3 g of molybdenum trioxide and 475 ml of cyclooctane is heated to 118° C. To this mixture is added 130 g (1.01 mol) of 70% aqueous tert-butyl hydroperoxide during a 5-hour period. The reaction mixture is maintained at reflux during the addition period, and water is collected in a Dean-Stark trap. The red reaction mixture is heated at reflux for 7 hours after the addition is complete to discharge the red color. The solids are removed by filtration and the filtrate is evaporated to give a yellow oil. Purification (Waters Prep 500A HPLC, 20:1 hexane:ethyl acetate) affords 78.7 g (68% yield) of the title compound as a colorless syrup.

Anal. Calcd. for $C_{44}H_{80}N_2O_6$: C, 72.1; H, 11.0; N, 3.8. Found: C, 72.0; H, 11.0; N, 3.7.

EXAMPLE 44

Di-(1-benzyloxy-2,2,6,6-tetramethylpiperidin-4-yl) Sebacate

A mixture of 20.0 g (41.6 mmol) of di-(2,2,6,6-tetramethylpiperidin-4-yl) sebacate, 300 mg of molybdenum trioxide and 110 ml of toluene is heated to 110° C. To this mixture is added 37.2 g (289 mmol) of 70% aqueous tert-butyl hydroperoxide over a 40-minute period. Water is collected in a Dean-Stark trap. The reaction mixture is heated at reflux for 12 hours. The orange mixture is then treated with 4.5 g (35 mmol) of fresh 70% aqueous tert-butyl hydroperoxide and 10 ml of toluene. The mixture is heated for another 3 hours to discharge the orange color. The reaction mixture is passed through silica gel with 2:1 hexane:ethyl acetate. The organic solution is washed with 10% sodium sulfite, with water, dried over anhydrous magnesium sulfate, and then evaporated to give a yellow oil. Purification (Waters Prep 500A; silica gel; 100:7 hexane:ethyl acetate) affords 7.0 g (24% yield) of the title compound as a white solid, m.p. 58°–61° C.

Anal. Calcd. for $C_{42}H_{64}N_2O_6$: C, 72.8; H, 9.3; N, 4.0. Found: C, 73.0; H, 9.8; N, 4.0.

EXAMPLE 45

Di-(1-octyloxy-2,2,6,6-tetramethylpiperidin-4-yl) Sebacate

A mixture of 15.0 g (31.2 mmol) of di-(2,2,6,6-tetramethylpiperidin-4-yl) sebacate, 0.7 g of molybdenum hexacarbonyl and 115 ml of n-octane is heated to 115° C. To this mixture is added 21.9 g (219 mmol) of 90% aqueous tert-butyl hydroperoxide over a 30-minute period. The reaction mixture is maintained at reflux during the addition and water is collected in a Dean-Stark trap. The red reaction mixture is heated at reflux for 6 hours after the addition is complete. The orange mixture is cooled to 60° C., treated with 3.5 g (35 mmol) of fresh 90% aqueous tert-butyl hydroperoxide and 20 ml of n-octane, and heated at reflux for an additional hour to discharge the color. The reaction mixture is filtered to remove solids, and then diluted with 100 ml of ethyl acetate and washed with a solution of 10 g of sodium sulfite in 200 ml of water. The aqueous wash is extracted with ethyl acetate and the combined organic solutions are washed once with water and then evaporated. The crude yellow liquid residue is purified by passing it through 220 g of silica gel with 100:7 heptane:ethyl acetate as eluent to afford 15.5 g (67% yield) of the title compound as a colorless oil. The oil has the same LC retention time as the compound prepared in Example 31.

EXAMPLE 46

Di-(1-octyloxy-2,2,6,6-tetramethylpiperidin-4-yl) Sebacate

A mixture of 15.0 g (31.2 mmol) of di-(2,2,6,6-tetramethylpiperidin-4-yl) sebacate, 0.2 g of chromium (VI) oxide, and 120 ml of n-octane is heated to 115° C. To the above mixture is added 28.5 g (221 mmol) of 70% aqueous tert-butyl hydroperoxide over a 90-minute interval while the reaction mixture is heated at reflux. Water is collected in a Dean-Stark trap. The red mixture is heated at reflux for 3.25 hours after the addition is complete in order to discharge the color. The reaction mixture is passed through 150 g of silica gel with 2:1 heptane:ethyl acetate as the eluent. The organic solution is evaporated to obtain a yellow liquid which is purified (Waters 500A HPLC; silica gel; 20:1 hexane:ethyl acetate) to afford 15.3 g (67% yield) of the title compound. The product has the same LC retention time as the compound prepared in Example 31.

What is claimed is:

1. A process for the preparation of an N-hydrocarbyloxy compound of the formula

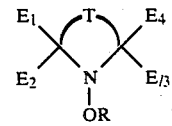

wherein the nitrogen atom is flanked by two quaternary carbon atoms where $E_1$ and $E_3$ are independently alkyl of 1 to 5 carbon atoms or phenyl, $E_2$ and $E_4$ are independently alkyl of 1 to 5 carbon atoms, or $E_1$ and $E_2$ together or $E_3$ and $E_4$ together or both $E_1$ and $E_2$ together and $E_3$ and $E_4$ together are tetramethylene or pentamethylene, R is a hydrocarbyl radical, and T is a divalent group required to form a cyclic 5- or 6-membered ring, T being inert to chemical change in the presence of hydroperoxide, which comprises dissolving a highly colored N-oxyl compound of the formula

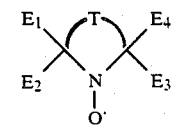

where $E_1$, $E_2$, $E_3$, $E_4$ and T have the meanings given above, in a hydrocarbon organic solvent, said hydrocarbon having at least one labile hydrogen atom and no ethylenic unsaturation, in the presence of a hydroperoxide and 0.001 to 0.1 mole percent, based on the hydroperoxide, of a catalyst selected from the group consisting of the metal carbonyls, the metal oxides, the metal acetylacetonates and the metal alkoxides where the metal is selected from groups IVb, Vb, VIb, VIIb and VIII of the periodic table, with the mole ratio of hydroperoxide to N-oxyl compound being 50:1 to 2:1, and heating the reaction mixture at a temperature of 50° to 200° C. for a period of time sufficient to discharge the color associated with the presence of N-oxyl compound and to form concomitantly the desired N-hydrocarbyloxy product.

2. A process according to claim 1 wherein $E_1$, $E_2$, $E_3$ and $E_4$ are each methyl.

3. A process according to claim 1 wherein R is alkyl of 1 to 18 carbon atoms, cycloalkyl of 5 to 12 carbon atoms, hydrocarbyl radical of a saturated bicyclic or tricyclic hydrocarbon of 7 to 12 carbon atoms, aryl of 6 to 10 carbon atoms, aralkyl of 7 to 13 carbon atoms or said aralkyl substituted by alkyl of 1 to 4 carbon atoms.

4. A process according to claim 3 wherein R is alkyl of 5 to 18 carbon atoms, cycloalkyl of 5 to 12 carbon atoms or aralkyl of 7 to 9 carbon atoms.

5. A process according to claim 4 wherein R is alkyl of 7 to 18 carbon atoms, cyclopentyl, cyclohexyl, cyclooctyl, cyclododecyl, methylcyclohexyl, alphamethylbenzyl or alpha,alpha-dimethylbenzyl.

6. A process according to claim 1 wherein the temperature is 75° to 160° C.

7. A process according to claim 1 wherein the mole ratio of hydroperoxide to amine is 10:1 to 2:1.

8. A process according to claim 1 wherein the hydroperoxide is tert-butyl hydroperoxide, tert-amyl hydroperoxide, ethylbenzene hydroperoxide or cumene hydroperoxide.

9. A process according to claim 7 wherein the hydroperoxide is tert-butyl hydroperoxide or cumene hydroperoxide.

10. A process according to claim 1 wherein the catalyst is vanadyl acetylacetonate, vanadium (III) acetylacetonate, cobalt carbonyl, chromium (VI) oxide, titanium tetrabutoxide, titanium (IV) isopropoxide, molybdenum hexacarbonyl or molybdenum trioxide.

11. A process according to claim 10 wherein the catalyst is chromium trioxide, molybdenum hexacarbonyl or molybdenum trioxide.

* * * * *